(12) United States Patent
Liu et al.

(10) Patent No.: US 8,795,988 B2
(45) Date of Patent: Aug. 5, 2014

(54) PRIMER-EXTENSION BASED METHOD FOR THE GENERATION OF SIRNA/MIRNA EXPRESSION VECTORS

(75) Inventors: Lin Liu, Edmond, OK (US); Deming Gou, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 1044 days.

(21) Appl. No.: 12/192,356

(22) Filed: Aug. 15, 2008

(65) Prior Publication Data

US 2009/0087910 A1    Apr. 2, 2009

Related U.S. Application Data

(60) Provisional application No. 60/956,619, filed on Aug. 17, 2007.

(51) Int. Cl.
| | |
|---|---|
| *C12P 19/34* | (2006.01) |
| *C12N 15/10* | (2006.01) |
| *C12N 15/11* | (2006.01) |
| *C12N 15/66* | (2006.01) |
| *C12N 15/64* | (2006.01) |

(52) U.S. Cl.
CPC ........ *C12N 15/111* (2013.01); *C12N 2310/111* (2013.01); *C12N 2330/30* (2013.01); *C12N 15/10* (2013.01); *C12N 2310/53* (2013.01); *C12N 15/66* (2013.01); *C12N 15/64* (2013.01); *C12N 2310/14* (2013.01)
USPC ...................................................... 435/91.1

(58) Field of Classification Search
USPC ...................................................... 435/91.1
See application file for complete search history.

(56) References Cited

PUBLICATIONS

Rossi et al. (Journal of Biological Chemistry, 1982 (257) pp. 9226-9229).*
McIntyre et al. Additional File 2. (BMC Biotech 2006, one page).*
Zeng et al. (Methods in Enzymology 2005 (392) pp. 371-380).*
Gou, et al., "Primer extension-based method for the generation of a siRNA/miRNA expression vector", "Physiol Genomics", Sep. 5, 2007, pp. 554-562, No. 31, Publisher: American Physiological Society, Published in: US.
Hernandez, et al., "Analysis of T-Cell Development by Using Short Interfering RNA to Knock Down Protein Expression", "Methods in Enzymology", 2005, pp. 199-217, vol. 392, Publisher: Elsevier, Published in: US.
Kim, et al., "Synthetic dsRNA Dicer substrates enhance RNAi potency and efficacy", "Nature Biotechnology", Feb. 2005, pp. 222-226, vol. 23, No. 2, Publisher: Nature Publishing Group, Published in: US.
Kim, et al., "A Simple and Economical Short-oligonucleotide-based Approach to shRNA Generation", "Journal of Biochemistry and Molecular Biology", Jan. 19, 2006, pp. 329-334, vol. 39, No. 2, Publisher: Department of Biomedical Science and Institute of Bioscience and Biotechnology, Published in: KR.
Luo, et al., "Small interfering RNA production by enzymatic engineering of DNA (SPEED)", "PNAS", Apr. 13, 2004, pp. 5494-5499, vol. 101, No. 15, Publisher: The National Academy of Sciences, Published in: US.
McIntyre, et al., "Design and cloning strategies for constructing shRNA expression vectors", "BMC Biotechnology", Jan. 5, 2006, pp. 1-8, vol. 6, No. 1, Publisher: BioMed Central, Published in: US.
Miyagishi, et al., "Optimization of an siRNA-expression system with an imroved hairpin and its significant suppressive effects in mammalian cells", "The Journal of Gene Medicine", Jan. 2, 2004, pp. 715-723, vol. 6, Publisher: Wiley InterScience, Published in: US.
Paddison, et al., "A resource for large-scale RNA-interference-based screens in mammals", "Letters to Nature", Mar. 2004, pp. 427-431, vol. 428, Publisher: Nature Publishing Group, Published in: US.
Paul, et al., "Effective expression of small interfering RNA in human cells", "Nature BioTechnology", May 2002, p. (s) 505-508, vol. 29, Publisher: Nature Publishing Group, Published in: US.

* cited by examiner

*Primary Examiner* — J E Angell
(74) *Attorney, Agent, or Firm* — Fellers, Snider, Blankenship, Bailey & Tippens, P.C.; Terry L. Watt

(57) ABSTRACT

Functional shRNA is produced from an expression vector prepared by selecting a two primer design in which the primers are less than about 50 nucleotides in length, annealing and extending the primers using primer extension, digesting the primer extension product and inserting the digestion product into a suitable vector. When the shRNA vectors are inserted into a cell, shRNA transcribed from the vectors modulates gene activity within the cell.

4 Claims, 9 Drawing Sheets

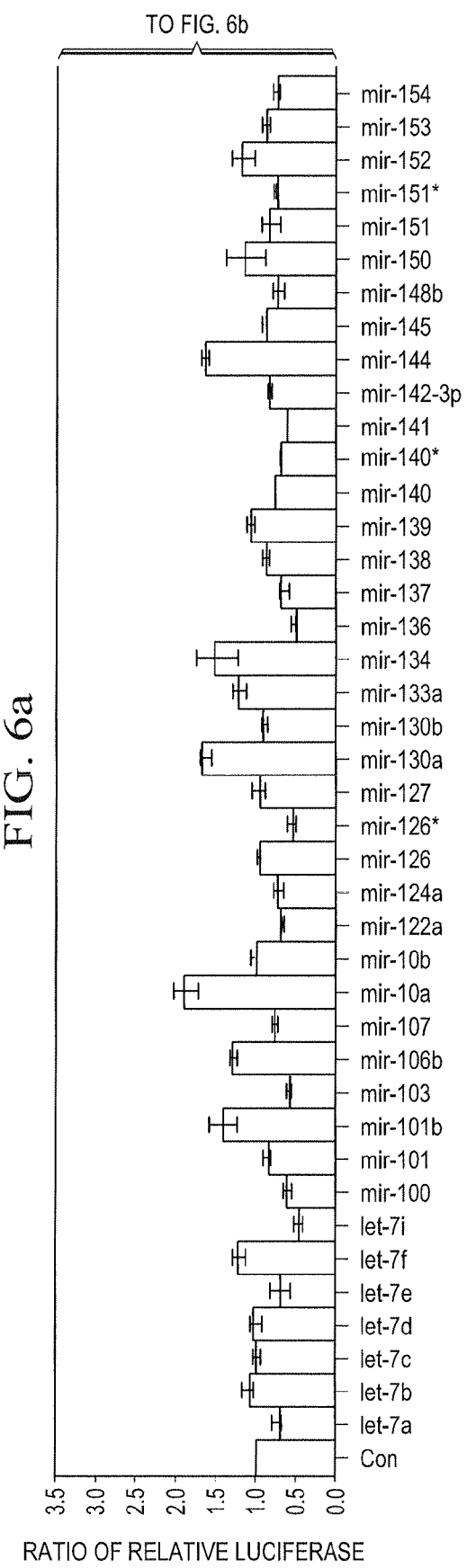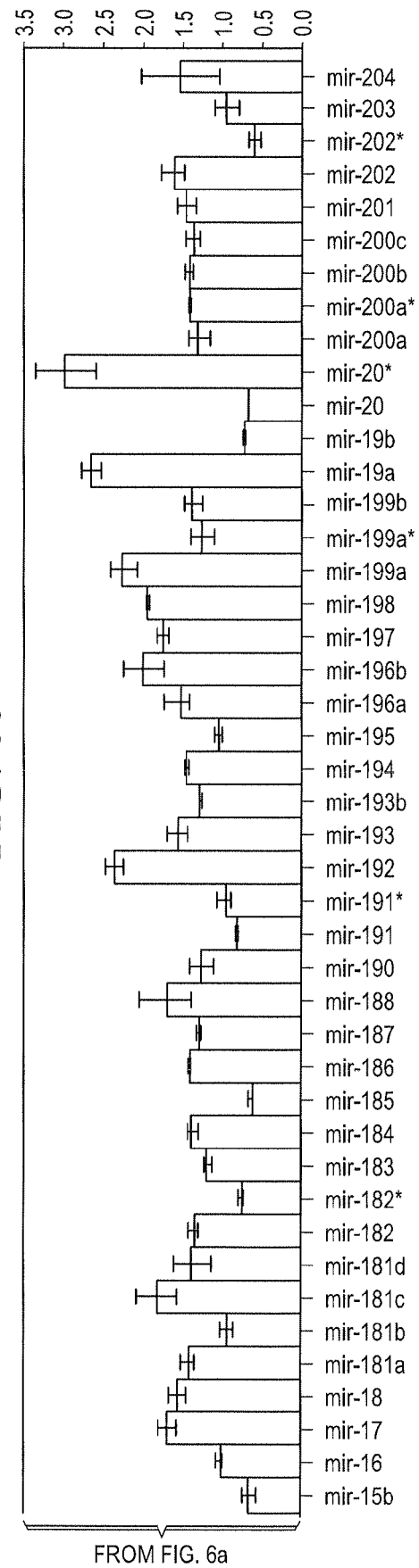
FIG. 6a
FIG. 6b

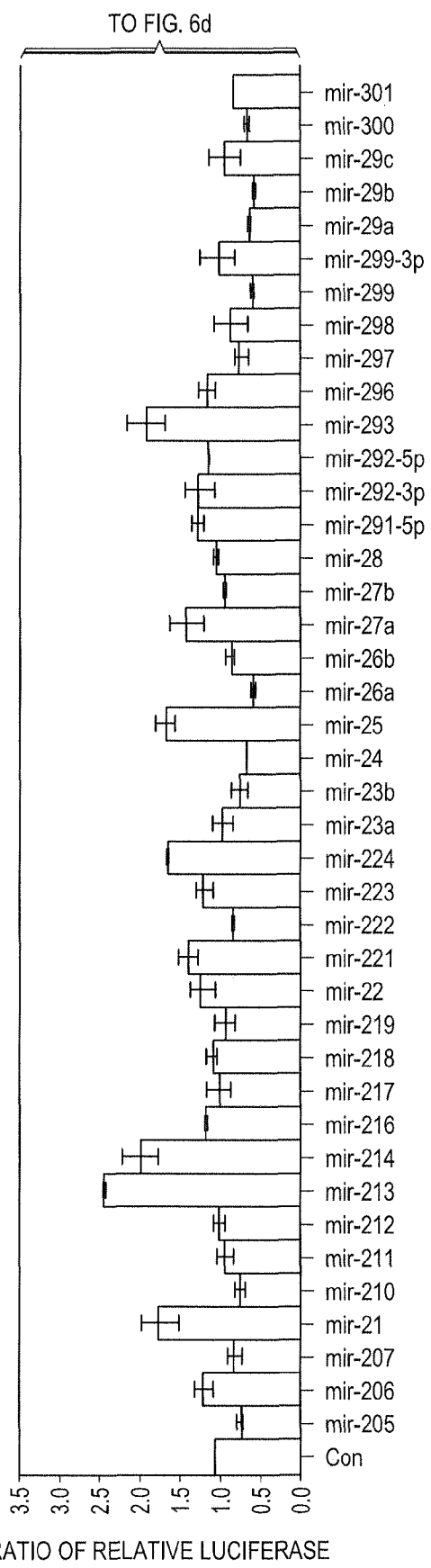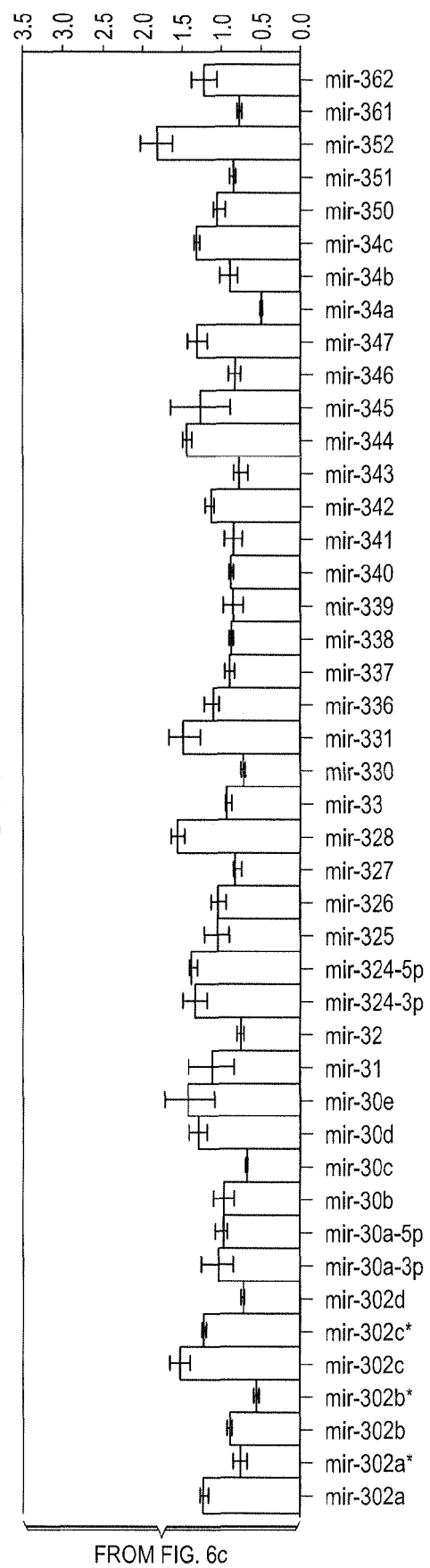

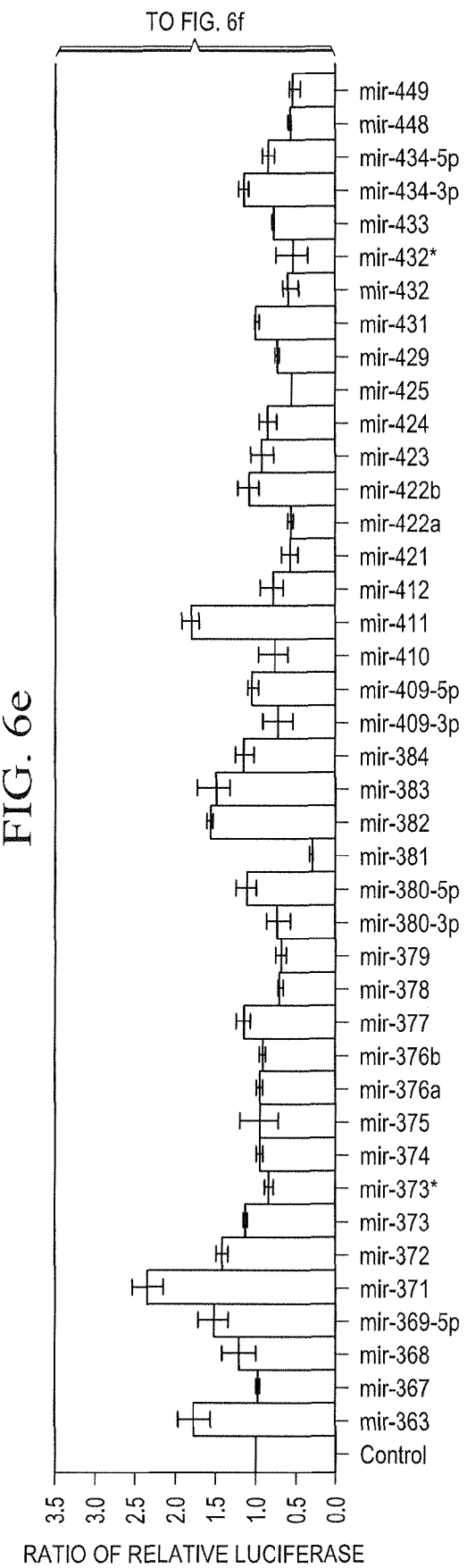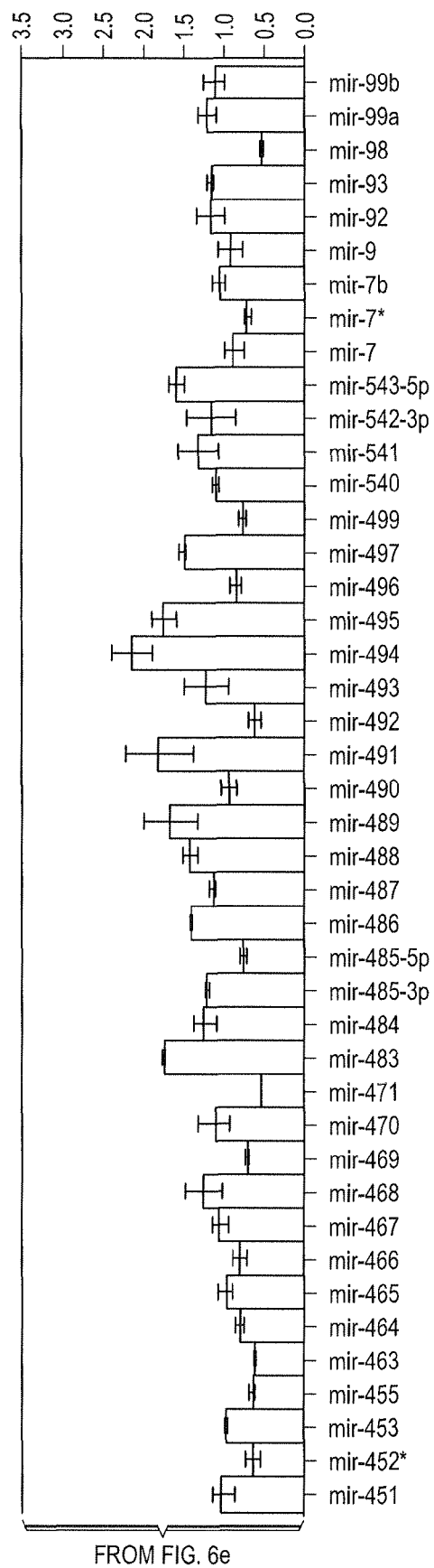
FIG. 6e
FIG. 6f

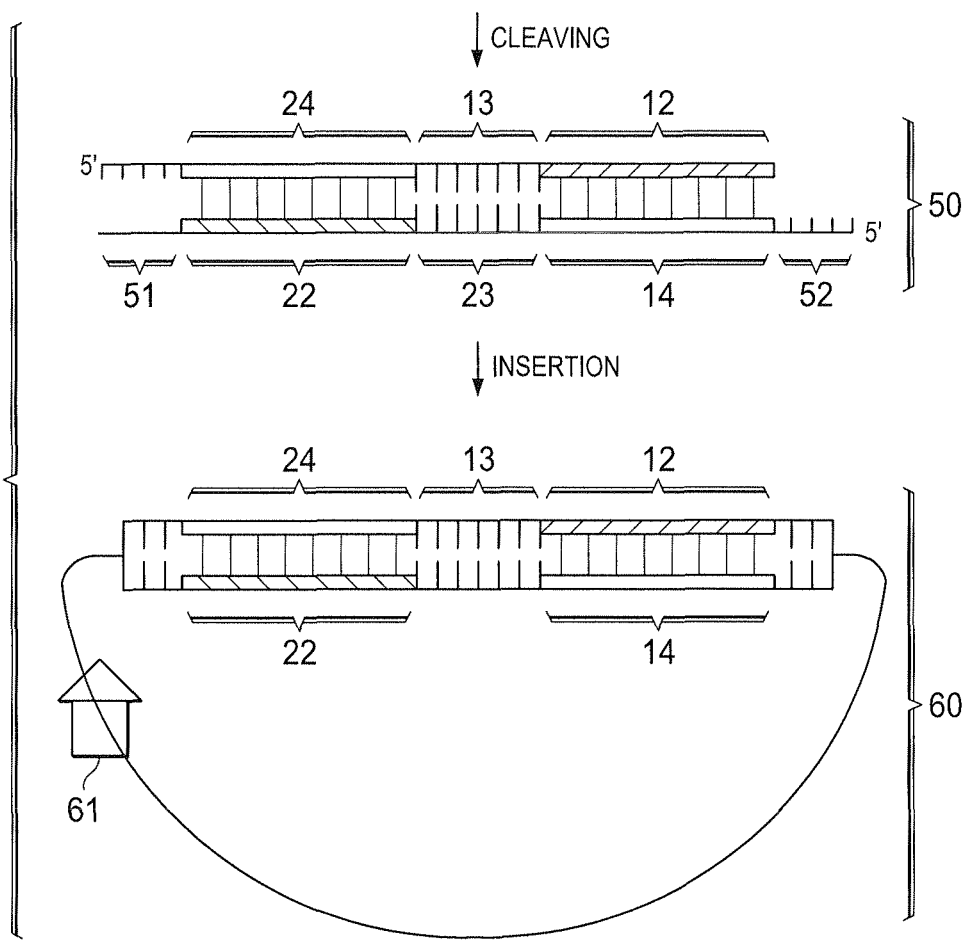
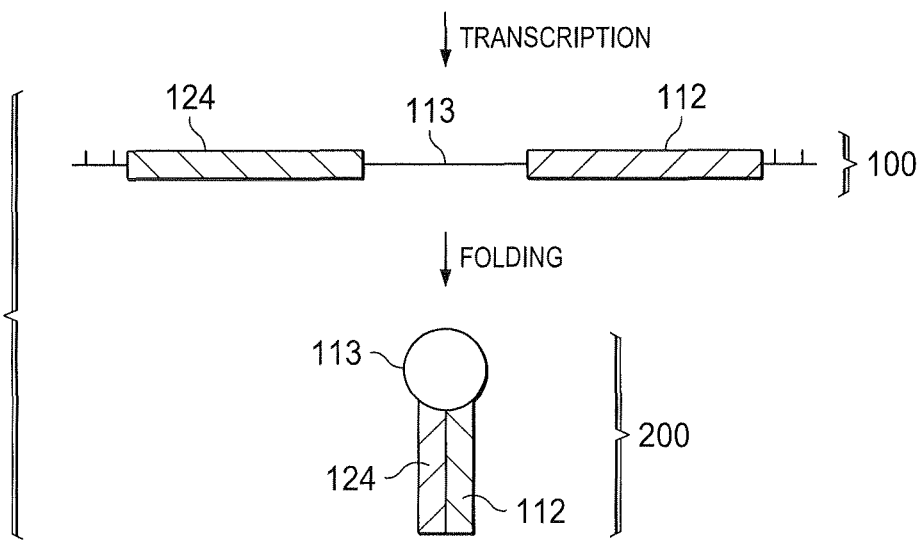
FIG. 7b
FIG. 7c

PRIMER-EXTENSION BASED METHOD FOR THE GENERATION OF SIRNA/MIRNA EXPRESSION VECTORS

CROSS-REFERENCE TO RELATED APPLICATIONS

This application claims benefit of U.S. provisional patent application 60/956,619, filed Aug. 17, 2007, the complete contents of which is hereby incorporated by reference.

STATEMENT REGARDING FEDERALLY SPONSORED RESEARCH OR DEVELOPMENT

This invention was made with government support under contracts R01 HL-052146, R01 HL-071628 and R01 HL-083188 awarded by the National Institute of Health. The government has certain rights in the invention.

SEQUENCE LISTING

This application includes as the Sequence Listing the complete contents of the accompanying text file "Sequence.txt", created Aug. 13, 2008, containing 4,571 bytes, hereby incorporated by reference.

BACKGROUND

Over the last few years, RNA interference (RNAi) has emerged as an effective method of silencing gene expression in a variety of organisms, particularly mammals (19). Among its many applications are the characterization and regulation of gene function, analysis of signaling pathway and target validation. Another intriguing aspect of RNAi is its potential therapeutic value. The RNAi response in mammalian cells mediated by dsRNA is a well-defined two-step process. Initially, the dsRNA is cleaved into small interfering RNAs (siRNA) of approximately 19 to 25 nucleotide (nt) by an RNase III-like enzyme known as Dicer. Then, the siRNA is incorporated into a RNA-induced silencing complex (RISC), which destroys mRNAs that are homologous to the integral siRNA (45). In mammalian cells, interferon-mediated antiviral response to long dsRNA (>30 bp) causes the global shutdown of protein synthesis. To bypass this non-specific effect, small siRNA (<30 nt) has been used to induce reliable and efficient knockdown of target genes while evading the interferon response (13).

Gene silencing can be induced by direct transfection of cells with chemically synthesized (13) or in vitro transcribed siRNA (24, 30, 33). Alternatively, it can be obtained by transfecting a plasmid or transducing a viral vector encoding a short hairpin RNA (shRNA) driven by a RNA polymerase (pol) III promoter, including U6, H1, 7SK and tRNA promoters (5, 15, 38, 43), or a pol II promoter such as CMV or SP-C (16, 42). shRNAs consist of short inverted repeats separated by a small loop sequence and is rapidly processed by the cellular machinery into 19-22 nt siRNA, thereby suppressing the target gene expression. Though siRNA and shRNA elicit comparable results in RNAi experiments, the use of shRNA expression vectors is more appealing with several advantages over chemically synthesized siRNA. First, the use of plasmid to express shRNA is fairly inexpensive and has been shown to achieve long-term target gene suppression in cells and whole organisms. Second, the efficient delivery and stable integration of these shRNA expression cassettes into the host genome can be efficiently achieved by using various viral systems. Third, inducible or cell-specific gene silencing can be obtained in vivo by using a DNA-based shRNA vector. Fourth, vector-based RNAi can be used to rapidly generate knockdown/knockout mice, which would be useful models for unraveling the genetic roots of many human diseases. In the past few years, various groups, including our own, have developed systems for vector-mediated specific RNAi in mammalian cells. Regarding the construction of shRNA vector, the most common strategy requires the synthesis, annealing and ligation of two complementary oligonucleotides encoding a desired shRNA target sequence into an expression vector (32). The small DNA inserts prepared from the annealed oligonucleotides consist of 19-29 nt complimentary to the target sequence followed by its antisense sequence placed in the inverse orientation, separated by a spacer to make the hairpin loop. A terminal signal of 5-6 T and the corresponding overhangs for cloning are also included. Although this method is quick, it often suffers from mutation problems (32, 37). Typically, 20-50% of cloned shRNA constructs contain significant mutations as determined by DNA sequencing. The mutation frequency is close to 75% when the desired siRNA sequence is 29 nt in size (37). The unreliability of this method is in part due to the errors in the synthesis of long oligonucleotides (>50-mer). To verify the shRNA constructs that do not contain any errors, it was advised to pick up at least a few bacterial colonies for sequencing (38). Obviously, this process is time-consuming and costly. Another strategy that fewer people use in constructing shRNA vector is a PCR approach. With this approach, a promoter sequence serves as the template with an upstream primer that is complementary to the 5' end of the promoter region, and a downstream primer containing the desired hairpin siRNA target sequence and a region that is complementary to the 3' end of the promoter (22). Although it allows successful amplification of hairpin structures in a single amplification step, the correct amplicon production is critically dependent upon on the quality of downstream primer. For this reason, the method requires costly purification of the long downstream primer. shRNA expression vector can also be produced from target cDNA by enzymatic digestion (30). However, this method involves a multi-step process and may increase off-target effects. Recently, McIntyre and Fanning (31) reported an alternative approach to construct shRNA expression vector through the primer extension using a long template oligonucleotide and a short universal primer. The mutation rate was decreased by using DNA polymerase Phi29. However, the method still utilizes one long template oligonucleotide (72 nt if the siRNA sequence is 21 nt), which is not a trivial task. The strong secondary structure within this long oligonucleotide led to the difficulty of chain elongation. Kim et al. (25) described another approach of generating shRNA with short oligonucleotides. It is more cost-effective and less error-prone, but the shRNA vector coming from this method may be less potent because the loop sequences must be palindromic.

As can be seen, current methods of constructing shRNA vectors are costly and often suffer from mutation problem during synthesis.

SUMMARY OF THE INVENTION

In the present disclosure, we report novel methods to design and produce shRNA expression vectors or templates with high efficiency. A major improvement was using shorter (≤50-nt) primers to generate a shRNA insert using primer extension. We found that the construction of shRNA expression vectors with this new approach dramatically reduces the occurrence of mutations. The methods allow the production of many shRNA vectors in parallel at a greatly reduced cost with high efficacy. Using this method, a microRNA (miRNA) overexpression library was constructed which facilitates the expression of 254 matured miRNAs that were candidates for involvement in human Survivin transcriptional regulation. High-throughput screening in A549 cells was performed. The results showed that the expression of several of the miRNAs (miR-192, 199a, 19a, 20a, 213 and 371) caused activation of the Survivin promoter while expression of several other miR-NAs (miR-302b*, 34a, 98, 381, 463 and 471) decreased Survivin promoter activity. These results show that the shRNA vectors of the invention can be successfully used to generate shRNAs (e.g. mature miRNAs) within cells and that the shRNA so-produced successfully modulates or regulates gene activity. The invention provides methods of making shRNA vectors, methods of making shRNA using such vectors, and method of modulating gene activity by expressing shRNA from the shRNA vectors within cells or tissues.

BRIEF DESCRIPTION OF THE DRAWINGS

FIG. 6A-G. Screening for miRNAs involved in the regulation of human Survivin promoter activity in A549 cells. A549 cells were plated 25000 cells/well in 96-well plates. After overnight culture, cells were transfected with 25 ng of pSurvivin-F. Luc reporter gene vector, 2.5 ng of pRL-TK normalization vector and 75 ng of each miRNA expression vector using Lipofectamine 2000. Forty-eight hours post-transfection, cells were assayed for dual-luciferase activities. The relative luciferase activities were normalized by a GFP control vector expressing unrelated shRNA (shCon). The results shown are means±S.D. (n=3). (G), Specificity of miRNAs in the promoter activity assay. Human SP-B promoter-driven firefly luciferase vector (pSP-B-F.Luc) was co-transfected with the pRL-TK vector and a miRNA over-expression vector. Forty-eight hours post-transfection, cells were assayed for dual-luciferase activities. The relative firefly luciferase activity in each treatment was normalized by a control vector expressing unrelated shRNA (shCon). The error bars indicated the standard deviation, n=3 in each group.

FIGS. 7A-C. Schematic representation of method for preparing shRNA. A, annealing and filling in steps; B, cleaving and insertion steps; C, transcription and folding steps.

DETAILED DESCRIPTION OF THE PREFERRED EMBODIMENTS

As described, over the last few years, RNA interference (RNAi) has emerged as an effective method of silencing gene expression in a variety of organisms, particularly mammal (16). Among its many applications are the characterization and regulation of gene function, signaling pathway analysis and target validation. Another intriguing aspect of RNAi is its potential therapeutic value. The RNAi response in mammalian cells mediated by dsRNA is a well-defined two-step process. Initially, the dsRNA is cleaved into small interfering RNAs (siRNA) of approximately 19 to 25 nucleotide (nt) by an RNase III-like enzyme known as Dicer. Then, the siRNA is incorporated into a RNA-induced silencing complex (RISC), which destroys mRNAs that are homologous to the integral siRNA (38). In mammalian cells, interferon-mediated antiviral response to long dsRNA (>30 bp) causes the global shut-down of protein synthesis. To bypass this non-specific effect, introducing small siRNA (<30 nt) has been used to induce reliable and efficient knockdown of target genes while evading the interferon response (10).

The present invention provides a new method of generating shRNA DNA vectors or templates for in vitro transcription. The method differs from prior art methods, for example, because the loop sequence of the shRNA is defined by two annealing oligonucleotides that are less than about 50 nt long. Since these short oligonucleotides extension reaction are less than 50 nt, and preferably less that about 45 nt long, the rate of mutation is sharply decreased and the accuracy of positive clones is dramatically improved. The method allows for the production of many shRNA vectors in parallel at a greatly reduced cost with high efficacy. By using the loop sequence-mediated primer extension method of the invention, a microRNA (miRNA) overexpression library was constructed that permitted the discovery of miRNAs that regulate promoter activity in the mammalian Survivin gene.

In one embodiment, the invention provides expression vectors encoding shRNA molecules of interest. Such vectors are typically plasmids, although those of skill in the art will recognize that other types of expression vectors may also be employed, including but not limited to various viral-based vectors such as adenoviral, lentiviral, adeno-associated viral, and retroviral vectors; as well as various plasmid-based vectors and other vectors such as baculovirus, phage, phagemids, cosmids, phosmids, bacterial artificial chromosomes, P1-based artificial chromosomes, yeast plasmids, yeast artificial chromosomes, etc. The vectors of the invention mediate the expression or over-expression (i.e. expression that would not occur if the vector was not present) of the shRNA molecules that they encode. Further, more than one shRNA may be encoded by a single expression vector. The shRNA that is encoded may function as siRNA, or as miRNA, etc.

Figure 7A:
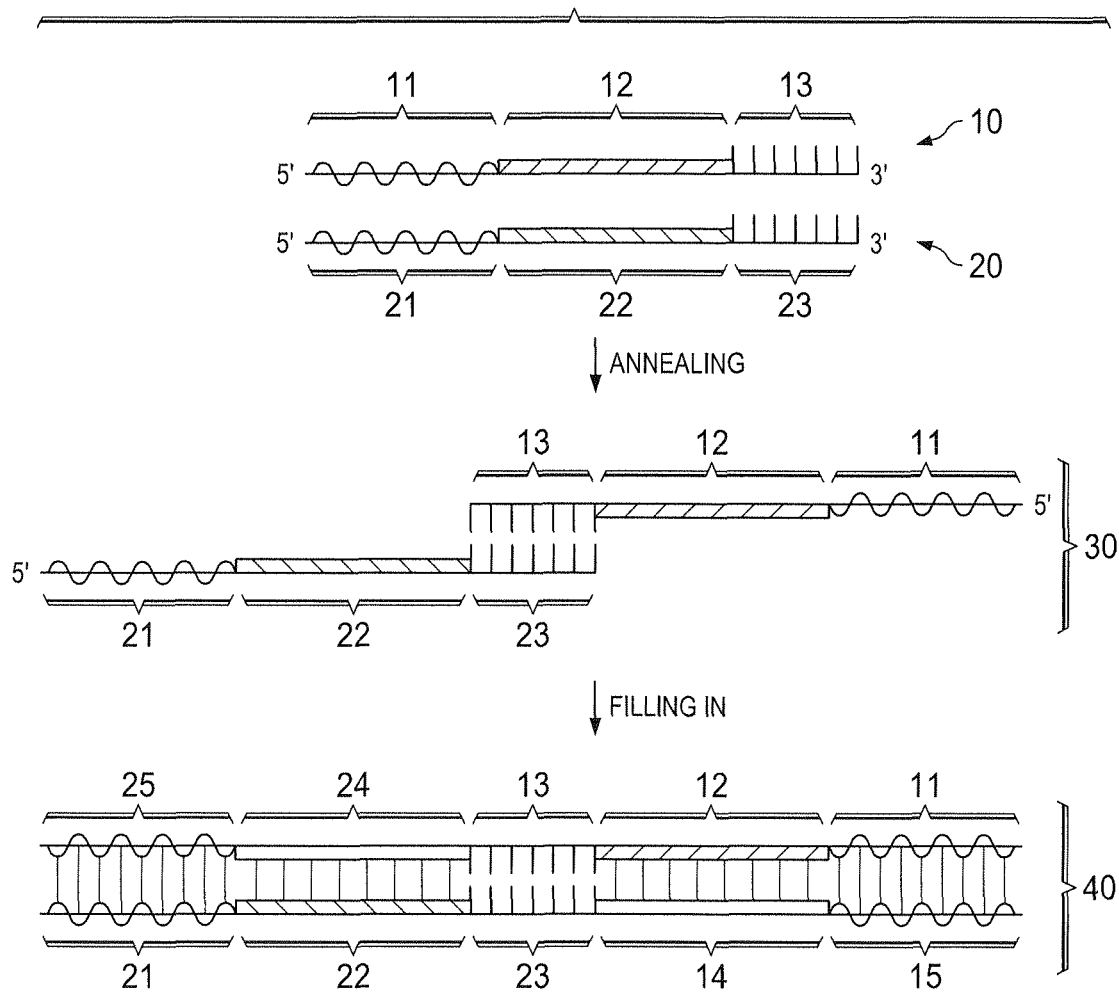

The vectors of the invention are made by designing and preparing two oligonucleotide primers (designated herein as the first and second primers, or as P1 and P2) that undergo annealing, conversion to double strand (ds) DNA, cleavage with restriction enzymes, and insertion into a suitable expression vector. Significantly, in order to minimize errors during primer synthesis, the length of each of the two primers is less than about 50 nucleotides (nts), and preferably is less than about 45 nts. Such primers include those with a total length of, for example, 50, 49, 48, 47, 46, or 45 or fewer nts. In order to accommodate the three basic elements that are encoded by the primers (described in detail below), the minimum length of the primers will be in the range of from about 36 to about 45 nts, and usually such primers will be at least about 36 nts in length. The two primers that are used in the preparation of a shRNA expression vector of the invention may both be the same length, or may differ in total length This procedure of preparing shRNA expression vectors using a two-primer design is represented schematically in FIGS. 7A-B, where primers 10 and 20 are indicated. With reference to FIG. 7A, primer 10 comprises at least three elements: element 11 which is or which includes a restriction enzyme recognition sequence; element 12, which is a sequence encoding the sense strand of an RNA stem structure; and element 13, which encodes an RNA loop structure. Primer 20 also comprises three elements: element 21 is or includes a restriction enzyme recognition sequence; element 22 is a sequence encoding the sense strand of an RNA stem structure and is the same as (i.e. is identical to) element 12 of primer 10; and element 23, which contains sequences that are complementary to the sequence of element 13. Therefore, when primers 10 and 20 contact one another under suitable conditions (conditions that allow base pairing to take place), segments 13 and 23 will anneal. This step of annealing results in the production of annealed structure 30. Annealed structure 30 is single stranded, except in the region of complementary base paired elements 13 and 23.

In addition, 10 and 20 primers 10 and/or 20 may include short optional protection sequences 5' and adjacent to one or both of elements 11 and 21. Such protection sequences are preferably of about 2 to about 5 nts in length. The function of a protection sequence is to increase the efficiency of restriction enzyme digestion.

The single strand portions or sections of annealed structure 30 are then "filled in" i.e. converted to double strand DNA, by the action of enzymes which are known to those of skill in the art, e.g. using Klenow fragment, Bst DNA polymerase large fragment, 9° Nm DNA polymerase, etc. Such enzymes attach an appropriate base to each base in a single stranded DNA sequence, thereby creating complementary sequences 14 (complementary to element 12), 24 (complementary to element 22), 15 (complementary to element 11) and 25 (complementary to element 21), to form double strand DNA structure 40. Those of skill in the art will recognize that various proofreading polymerases and enhancing agents may be included in this reaction in order to increase accuracy. Cleavage of ds DNA structure 40 using an appropriate restriction enzyme (i.e. restriction enzymes that recognize and cleave elements 11 and 21) results in production of structure 50 which contains 5' overhangs 51 and 52. Structure 50 can then readily be inserted into an expression vector such as a plasmid that has been cleaved or otherwise constructed so as to contain complementary overhangs, as is known to those of skill in the art.

The shRNA expression vectors of the invention may also include other features, including but not limited to: reporter genes such as Green fluorescent Protein (GFP), LacZ or red fluorescent protein; and various promoter (inducible or non-inducible) such as, for example, the Survivin promoter, H1, U6, 7SK, etc., to drive transcription of the shRNA and/or of other genes located in the vector. Further, the vector may be designed to contain, for example, tissue or cell specific promoters which cause transcription of the shRNA in a tissue or cell-specific manner. Within the expression vector, the sequences encoding one or more shRNA molecules are expressibly linked to a promoter, i.e. they are located within the expression vector in a manner that allows transcription of the shRNA to be initiated or driven by the promoter in a manner that produces functional shRNA. Functional shRNA is shRNA that attains a secondary structure (e.g. via base pairing, folding, etc.) that is capable of biological activity, i.e. of regulating or modulating gene activity, when suitable homologous or complementary nucleotide sequences are present (e.g. within a cell) and is allowed to interact with the shRNA.

Transcription of vector 60 by techniques that are known to those of skill in the art produces single strand RNA 100. ssRNA 100 comprises sequence 124, which corresponds to element 22 of original primer 20, sequence 112, which corresponds to element 12 of original primer 10, and sequence 113, which corresponds to element 13 of primer 10. Because elements 12 and 22 of primers 10 and 20 are identical, after the steps of annealing, filling in, cleaving, insertion and transcription, sequences 124 and 112 are complementary to one another. Under conditions favorable to RNA base pairing, these two segments base pair (anneal) and folded shRNA structure 200 is formed. shRNA 200 includes ss loop 113, which is not base paired. Transcription reactions may take place in vitro or in vivo, in cells or in cell-free translation systems.

Those of skill in the art will recognize that, while in this schematic representation base pairing between complementary sequences is depicted as exact (i.e. depicted with no unpaired bases) this need not be the case. For example, additional paired or unpaired bases may be present at the 5' or 3' end of sequences 112 and/or 124. Such bases, which would typically be a maximum of about 5 nts in length, and preferably shorter, may originate e.g. from the restriction site sequences, or be introduced as an artifact of transcription, or originate from protection sequences, etc. Further, sequences 112 and 124 need not be completely complementary. For example, they may be substantially complementary, based paired over most of their length (e.g. more than about 75%, and preferably more than 80%, and more preferably more than 90% of the nts in each of strands 112 and/or 124 are base-paired with a nt from the opposite, largely complementary strand). Those of skill in the art will recognize that mismatches in the substantially complementary sequences may cause a single strand "bulge" in the stem of the stem-loop structure.

In addition, those of skill in the art will recognize that loop 113 need not be completely single stranded. In some embodiments, some base pairing within the loop may occur, and structures such as bulges or bubbles may be formed within the loop. Further, multiple loops may form within a single "loop" structure, or cloverleaf structures, etc. may be formed. However, generally those of skill in the art will recognize that at least the first 3' and 5' nucleotides, and usually at least the first two 3' and 5' nucleotides adjacent to the stem, will not be base-paired, and will define the beginning of the loop segment of the shRNA. In addition, if there is basepairing within the loop, generally fewer than about 20%, and typically fewer than about 15%, and more typically fewer than 10% of the bases in the loop will be base-paired.

The primers utilized in the practice of the invention are generally single strand DNA primers comprising the nucleotides adenine (A), cytosine (C), guanine (G) and thymine (T), as is well-known to those of skill in the art.

The primers of the invention comprise at least three elements: an element that encodes one or more restriction sites; and element that encodes RNA loop sequences, and an element that encodes an RNA stem-forming sequence. The primers themselves are typically less than about 50 nts, and preferably less than about 45 nts, in length. The sizes of the three elements may vary from construct to construct, but will generally be as follows: the sequences that contain at least on restriction site are from about 6 to about 12 nts in length; the sequences that encode an RNA loop sequence are generally from about 3 to about 19 nts in length, and are preferably greater than about 7 nts in length; and the sequences that encode an RNA stem sequence are from about 15 to about 25 nts in length, and preferably from about 19 to about 22 nts in length. Depending on the construct, the loop structure may be about 3, 4, 5, 6, 7, 8, 9, 10, 11, 12, 13, 14, 15, 16, 17, 18, 19, or 20 nts in length.

Those of skill in the art will recognize that many restriction enzymes exist, the corresponding restriction enzyme recognition sites of which may be incorporated into the primers of the invention. Preferably, the restriction sites that are used produce 3' and/or 5' overhangs upon cleavage with an appropriate restriction enzyme. Examples of such restriction enzymes include but are not limited to Eco31I, Bsp119I, XhoI, EcoRI, ApaI, BamHI, BglII, ClaI, HindIII, SalI, XbaI, etc.

Selection of the sequences that are included in the stem portion of the shRNA are selected based on the intended use of the shRNA. Generally, sequences in the stem are complementary to a sense and antisense DNA of interest, such as a gene, and are from about 15 to 25 nts in length, preferably from about 19 to about 22 nts in length, and more preferably from about 20 to about 21 nts in length. By base-pairing with the gene, transcription of the gene, and thus translation of the encoded protein) is prevented. In this manner, shRNA molecules can inhibit expression or activity of a gene of interest and the protein it encodes. In one aspect of the invention, an array or library of shRNA vectors may economically and easily be produced and used to interrogate a cell or cells or tissues to investigate the effect of the inhibition of one or more genes at once, or to investigate the effect of one or more shRNAs on one or more genes. For example, such investigations may be carried out in a high throughput screening format. Further, such shRNA molecules may mimic naturally occurring molecules that have or contain stem loop structures, such as microRNA (miRNA). Inhibition reactions with either a single type of shRNA or with multiple shRNAs (e.g. a library) may be carried out in vitro or in vivo, as well as in cell-free translation systems.

The single strand loop of the shRNA is typically from about 3 to about 19 nts in length, and preferably is greater than about 7 nts in length. The composition of the loop may be selected, for example, from structures that are available in the extant literature, or modifications thereof. In other words, the loop sequences may be identical to loop sequences that are known to occur in nature, or, alternatively, they may be modified versions of naturally occurring loop sequences. Finally, the loop sequences may be designed artificially (i.e. de novo) without reference to naturally occurring sequences. In addition, it is possible to "mix and match" natural or artificial loop structures with natural or artificial stem structures.

The shRNA vectors and shRNA molecules described herein contain various nucleic acid sequences that are complementary to various other nucleic acid sequences, e.g. within the same molecule or structure (e.g. the stem portion of an shRNA, the annealing region of the annealed structure, etc.). Those of skill in the art will recognize that due to the base-pairing nature of nucleic acids and the ability of a single strand of nucleic acid to serve as a template for production of a corresponding complementary strand of nucleic acid, which in turn may serve as a template for production of another complementary strand, a pattern or particular sequence of nucleotide bases that is introduced (e.g. in a primer) may be passed from one nucleic acid to another during replication, extension reactions, amplification, etc. As used herein, sequences which are related to one another in this manner may be referred to as homologous sequences or corresponding sequences. Such sequences may or may not be complementary.

EXAMPLES

Example 1

Construction of siRNA/miRNA Expression Vectors Using Primer-Extension

MicroRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression. In this example, a library of shRNA molecules comprising sequences of known miRNAs was constructed and used in a high throughput screening format to test the ability of each shRNA/miRNA in the library to influence the activity of the Survivin promoter.

Materials and Methods

Figure 1:
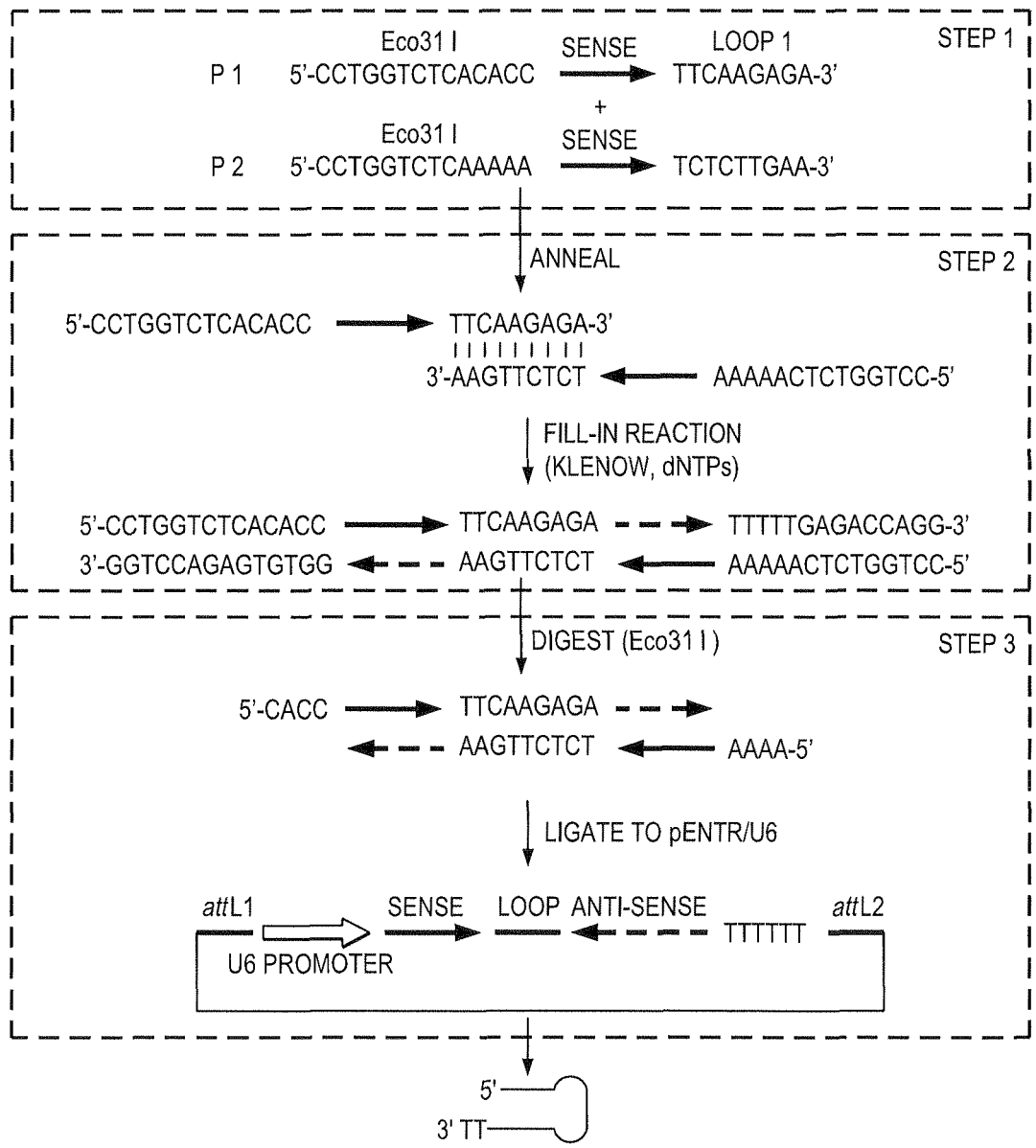
FIG. 1. Overview of the primer extension method used to produce short hairpin DNA inserts for the construction of shRNA vector. Step 1, Rule of two primer design; Step 2, Primer annealing and extension; Step 3, Digestion of primer extension product to leave the overhang sequences of 5'-CACC and 5'-AAAA for the ligation with the pENTR/U6 vector.

Construction of shRNA expression vector using primer extension. Here, we describe the approach of making a human U6 promoter driven shRNA vector with the most recommended loop sequence of 5'-TTCAAGAGA-3'. The entire procedure involves the following four steps as shown in FIG. 1.

Step 1: Primer design. To make a small DNA fragment containing sense-loop-antisense-terminal signal and the corresponding cloning sites, two oligonucleotides were designed for primer extension. The sequence of upper (P1) oligonucleotide includes 5'-CCTGGTCTCACACC[G]$N_{(19-23)}$TTCAAGAGA-3' (SEQ ID NO:5); the lower oligonucleotide includes 5'-CCTGGTCTCAAAAA$N_{(19-23)}$TCTCTTGAA-3' (SEQ ID NO: 6). Minimal synthesis oligonucleotides (0.025 µM and desalt) were obtained from Sigma Genosys and re-suspended in TE buffer (10 mM Tris pH 8.0, 1 mM EDTA) at the concentration of 50 µM. Since the sizes of all oligonucleotides were less than 50-nt, their accuracy during the synthesis is guaranteed by the company.

Step 2: Primer extension. Twenty five picomoles of each oligonucleotide was used in the extension reaction including 1× buffer G (Fermentas), 0.2 mM final concentration of dNTPs, and 1 unit of Klenow fragment (3'→5' exo-). The reaction was carried out at 37° C. for 30 min and then the Klenow was inactivated at 70° C. for 20 min.

Step 3: Digestion, purification, ligation and transformation. After heat inactivation of the Klenow Fragment, 5 U of Eco31 I (Fermentas) were directly added into the reaction. After digestion at 37° C. for 2 h and purification was carried out using a QIAEX II Gel Extraction Kit (Qiagen). 100 ng of purified DNA inserts were ligated into pre-made pENTR/mU6 vector (see below). Positive clones were confirmed by automated sequencing using U6-sequencing primer (5'-GGACTATCATATGCTTACCG-3', SEQ ID NO: 7).

Construction of miRNA Overexpression Library

The mU6 promoter was amplified from the pSilencer 1.0 vector (Ambion) with the primers 5'-CACCGCGGATC-GATCCGACGCCGCCATCTCTA-3' (SEQ ID NO: 8) and 5'-CTTCGAAGAATTCCCGGGTCTCTCAAA-CAAGGCTTTTCTCCAA-3' (SEQ ID NO: 9). The PCR products were directly cloned into the pENTR/D-Topo vector (Invitrogen), resulting in a pmU6 vector. Four restriction sites, including Bsp119 I, EcoR I, Sma I, and Eco31 I were introduced at the 3'-end of the mU6 promoter. For the convenience of monitoring transfection efficiency or determining virus titer, a CMV-driven EGFP expression cassette was introduced downstream of the mU6 promoter through Bsp119 I-Asc I sites (Asc I is in the pENTR vector). This resulted in a ready-to-use vector, pEGFP/mU6. Digestion of the pEGFP/mU6 vector with EcoR31 I and Bsp119 I left CAAA and CG 5'-overhangs, respectively. With an aim of over-expressing microRNA sequences in mammalian cells for functional screening, we selected 270 mature miRNA sequences in mammalian cells for a functional screen, 254 mature miRNA sequences were selected from the miRBase database located at microrna.sanger.ac.uk. A vector featuring a short hairpin microRNA (miRNA) structure was constructed. Similar to the construction of the RNAi vector, the above-described primer extension method was used to construct a DNA vector expression matured miRNA sense and its antisense sequences in the form of short hairpin RNA molecules. The 9-nt loop 5'-TTCAAGAGA-3' was replaced by a 10-nt loop sequence, 5'-CTTCCTGTCA-3' (SEQ ID NO: 10). The P1 oligonucleotide contained sequence 5'-CAAG-GTCTCATTTG (SEQ ID NO: 11), the mature-miRNA sense sequence 5'-CTTCCTGTCA-3' (SEQ ID NO: 12); the P2 oligonucleotide includes 5'-GAGTTCGAAAAA-3' (SEQ ID NO: 13) mature-miRNA sense sequence 5'-TGACAG-GAAG-3' (SEQ ID NO: 14). As two restriction site of Eco31 I and Bsp119 I, were included in the P1 and P2 oligonucleotides, respectively, (see underlining in FIG. 1, Step 1), the extension product resulted in 5'-TTTG and 5'-GC overhangs after digestion with Eco31 I and Bsp119 I, and could be directly inserted into the pEGFP/mU6 vector via corresponding sites. The ligation mixtures were transformed into chemically competent cells of GT116. All the inserts were verified by DNA sequencing with a mU6 sequencing primer (5'-ACATGATAGGCTTGGATTTC-3', SEQ ID NO: 15).

miRNA Library Screen

The 1.1 kb of Survivin promoter was amplified from human genomic DNA with a primer set of 5'-CACCGAGGC-CGCTGGCCATAGAACCAGAGAAGTGA-3' (SEQ ID NO: 16) and 5'-TAACTAGTCCACCTCTGC-CAACGGGTCCCGCG-3' (SEQ ID NO: 17) and subcloned into the previously described pENTR/CMV-EGFP vector (16) by switching CMV promoter through Not I and Spe I sites. Next, the EGFP fragment was replaced with Firefly luciferase, (F. Luc), which was amplified from a pGL3-control vector (Promega). The new vector of pSurvivinF.Luc was used for co-transfection combined with miRNA vectors and the normalization vector, pRL-TK (Promega). As an unrelated promoter control, the human SP-B promoter was amplified from human genomic DNA with the primer set: 5'-CAC-CGCGGCCGCGTATAGGGCTGTCTGGGA-3' (SEQ ID NO: 18) and 5'-GGACTAGTCTGCAGCCTGGGTAC-3' (SEQ ID NO: 19). The SP-B promoter-driven F.Luc vector, pSP-B-F.Luc was constructed by replacing the Survivin promoter with the SP-B promoter through Not I and Spe I sites. A549 human lung cancer cells were grown in F12K medium (Invitrogen) supplemented with 10% fetal bovine serum. Transient transfection of plasmids into overnight cultured A549 cells ($2.5 \times 10^4$ cells/well) in 96-well plates was performed for 48 h using Lipofetamine™ 2000 (Invitrogen). The transfected DNA mixtures (102.5 ng/well) contained 25 ng of pSurvivin-F.Luc, 2.5 ng of pRL-TK and 75 ng of miRNA over-expression vector. After 2 days of transfection, 10 of 50 µl of total cell lysate were used for determining luciferase activities by a luminometer and dual luciferase assay kit (Promega). The luciferase activities were normalized against the activity of pRL-TK control vector.

RNAi EGFP suppression assays. 293A cells were cultured in 24-well plates until >90% confluence. The cells were transfected with 50 ng of respective target pCMV-EGFP plasmid and 250 ng of shRNA expression vector by using Lipfectamine 2000 reagent (Invitrogen). To normalize the transfection efficiency, 50 ng of a red fluorescent protein reporter plasmid (pDsRed2-C1 vector, Clonetech) were co-transfected with each sample (12, 41). After 48 h, the cells were washed twice with PBS, 250 µl of lysis buffer was added to each well and the cells were freeze-thawed 3-times. After centrifugation for 10 min, 5 µl of supernatants were used to measure the expression of EGFP and DsRed2, which was determined by the FluoroMax 3 fluorometer using Ex=489 nm/Em=508 nm and Ex=563 nm/Em=582 nm, respectively.

Results and Discussion

Construction of shRNA Vector

Figure 2:
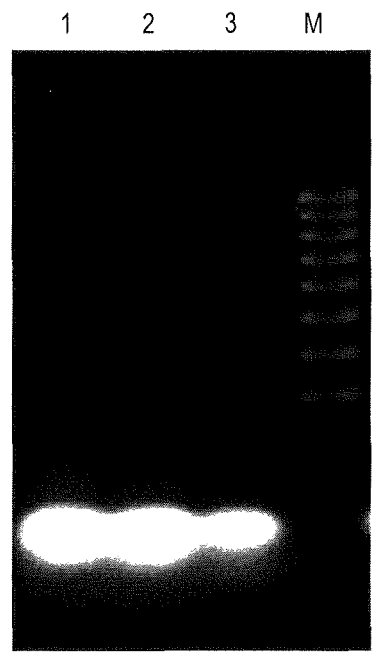
FIG. 2. Primer extension products by three different DNA polymerases. 5 µl of reaction products were analyzed on a 1.5% agarose gel in SB buffer. The products of 76 bp small DNAs were indicated by arrowhead. Lane 1, Klenow Fragment; Lane 2, Bst DNA polymerase large fragment; Lane 3, Taq DNA polymerase; Lane M, 100 bp DNA ladder.

To validate our approach, we selected a 21-nt siRNA sequence against the coding region of EGFP at the position of 417 to 437 (5'-GCACAAGCTGGAGTACAACTA-3', SEQ ID NO: 20). The reaction was carried out with 25 pmol of each primer and three DNA polymerases ranging in concentration from 0.5 U to 2.5 U in 20 µl of total volume. Primer extension products were analyzed on 1.5% Sodium Boric acid (SB) agarose gels. As shown in FIG. 2, primer extension with either Klenow Fragment (3'→5' exo-) or Bst DNA polymerase large fragment occurs effectively with a sharp DNA band of 76-bp in size. Taq DNA polymerase is less efficient, probably because the extension temperature of 72° C. is too high for primer annealing. When we checked the amount of each polymerase in a 20 µl of reaction volume, we found that 1.0 U of each polymerase is sufficient to produce enough DNA products.

Because the primer extension products need to be digested with a restriction enzyme before cloning into the shRNA vector, we therefore generated those extension products by using Klenow Fragment, which is active in all restriction enzyme reaction buffers. 5 U of Eco31 I was then added to the reaction mixtures that were heated at 75° C. for 20 min to inactivate the Klenow Fragment. After allowing the reaction to proceed at 37° C. for 2-4 h, we purified the Eco31 I digested DNA by using a QIAEX II Gel Extraction Kit. The purified DNA was ligated into the pre-prepared pENTR/mU6 vector and transformed into GT116 competent cells. For comparison, we also constructed shEGFP vectors by using the conventional method of two longer oligonucleotides. The final sequencing results showed that only 2 plasmids out of 40 samples coming from the primer extension method of the invention have mutations (Table 1), which is much lower than the number of mutations produced using the conventional annealed oligonucleotides cloning strategy, in which 32 out of 40 clones had mutations. This result shows that the novel method of the invention for producing siRNA/miRNA is significantly less error-prone than previously known methods.

| siRNA length | Loop sequence (5'→3') | Construction method | Mutation (out of 10 plasmid) |
|---|---|---|---|
| 21 | TTCAAGAGA | Annealed oligos | 3 |
|  |  | Primer-Extension | — |
| 21 | CTTCCTGTCA (SEQ ID NO: 1) | Annealed oligos | 2 |
|  |  | Primer-Extension | — |
| 21 | GTGTGCTGTCC (SEQ ID NO: 2) | Annealed oligos | 3 |
|  |  | Primer-Extension | 1 |
| 21 | TAGT<u>GAAGCCACAGA</u>TGTA (SEQ ID NO: 3) | Annealed oligos | 4 |
|  |  | Primer-Extension | 1 |

Table 1: Sequencing evaluation of shRNA vectors generated by primer-extension with two short oligos or by traditional method with two longer annealed oligos.[10] Plasmids from each group were randomly picked for DNA sequencing with U6 sequencing primer.

Figure 3A:
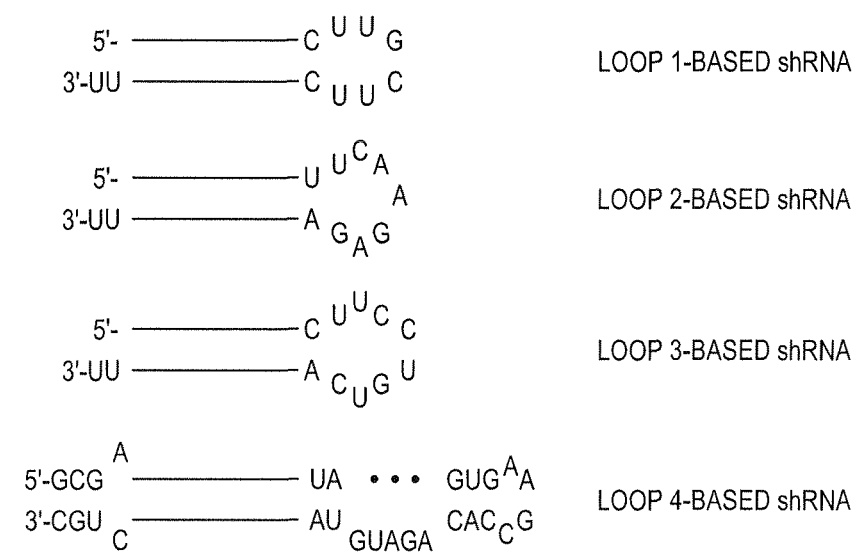
FIG. 3A-C. Effect of loop sequences on primer extension products and silencing efficiency. (A) The putative shRNA structures with 4 different loop sequences. (B) Four extension products with different loops by using Klenow fragment were analyzed on a 1.5% agarose gel in SB buffer. Lane M, 100 bp DNA ladder; Lane 1, 9-nt loop sequence of 5'-TTCAA-GAGA-3'; Lane 2, 10-nt loop sequence of 5'-CTTCCT-GTCA-3' (SEQ ID NO: 1); Lane 3, 11-nt loop sequence of 5'-GTGTGCTGTCC-3' (SEQ ID NO: 2); Lane 4, 19-nt loop sequence of 5'-TAGTGAAGCCACAGATGTA-3' (SEQ ID NO: 3; annealing region was underlined); Lane 5, negative control of two primers before extension. (C) Silencing of EGFP by vector-based shEGFP with different loop structures. 293A cells were co-transfected with U6-driven shEGFP417 with 4 different loop sequences and pDsRed2-C1 for normalization). The pU6-shFL vector expressing a shRNA against firefly luciferase (shCon) was used as a negative control. EGFP expression was shown as a percentage of shCon (means±SD, n=3).
Figure 3B:
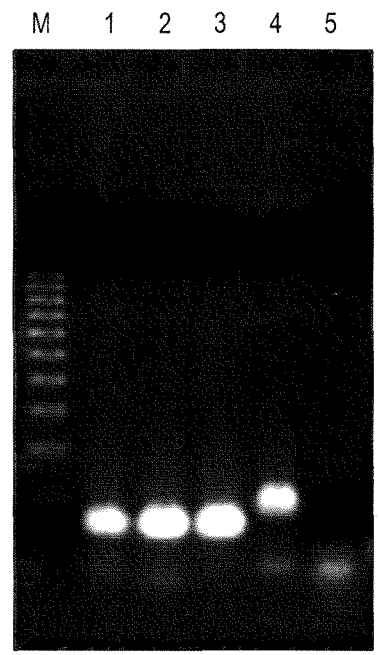

As this present method is based on loop sequence for the annealing of two primers, the selection of a loop sequence is the key of this procedure. In DNA-based RNAi studies, a short loop sequence is necessary for construction of shRNA expression vectors. Up to now, more than 20 different loop sequences, ranging in size (length) from 3-nt to 19-nt, have been reported. For example, Paul et al. used a 4-nt, 5'-UUCG-3', tetra nucleotide sequence (38); Sui et al. used 5'-CTCGAG-3' as a loop sequence (43); Agami's group uses a 9-nt loop sequence, 5'-TTCAAGAGA-3', (5). The loop sequence appears to somewhat influence the RNAi effect, To ensure the efficient annealing of two primers, we recommend using >7-nt loop sequence. In this report, we examined extension reactions carried out with four different loop sequences as follows: 8-nt of 5'-CTTGCTTC-3' (loop 1), 9-nt of 5'-TTCAAGAGA-3' (loop 2), 10-nt of 5'-CTTCCTGTCA-3' (loop 3, SEQ ID NO: 1) and 19-nt sequence of 5'-TAGTGAAGCCACAGATGTA-3' (loop 4, SEQ ID NO: 3) (FIG. 3A). To reduce the primer length during the synthesis of each oligonucleotides at small scale, only 10-nt in loop 4 (italicized) were selected as the annealing sequence in the extension reaction. However, all designs depicted gave successful extension products (FIG. 3B).

Figure 3C:
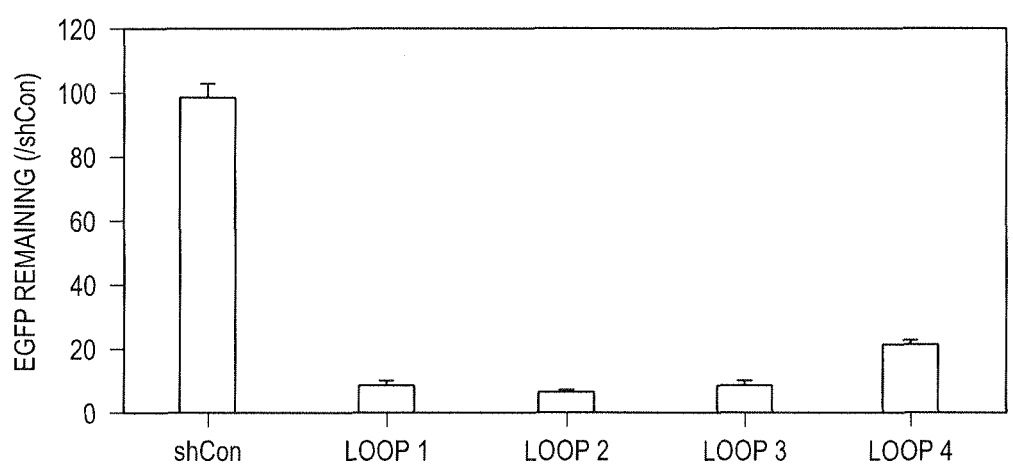

To study the possible influence of the loop sequences on the RNAi effect, we transfected 293A cells with each construct in combination with a homologous target expression plasmid pENTR/CMV-EGFP, which encodes EGFP, and with a non-targeted reporter plasmid pDsRed2-C1, which encodes the DsRed2 protein for normalization. As shown in FIG. 3C, the first three loop sequences have a similar activity in silencing EGFP. Human miR-30 (loop 4) mediated RNAi was less effective. This result differs from that of a previous study, in which the expression of HIV-1 specific shRNA through a miR-30 precursor stem-loop structure was shown to be approximately 80% more effective than loop 2-mediated shRNA (4). Although the reason for this difference is not clear, similar results have also been obtained by others (51).

Figure 4:
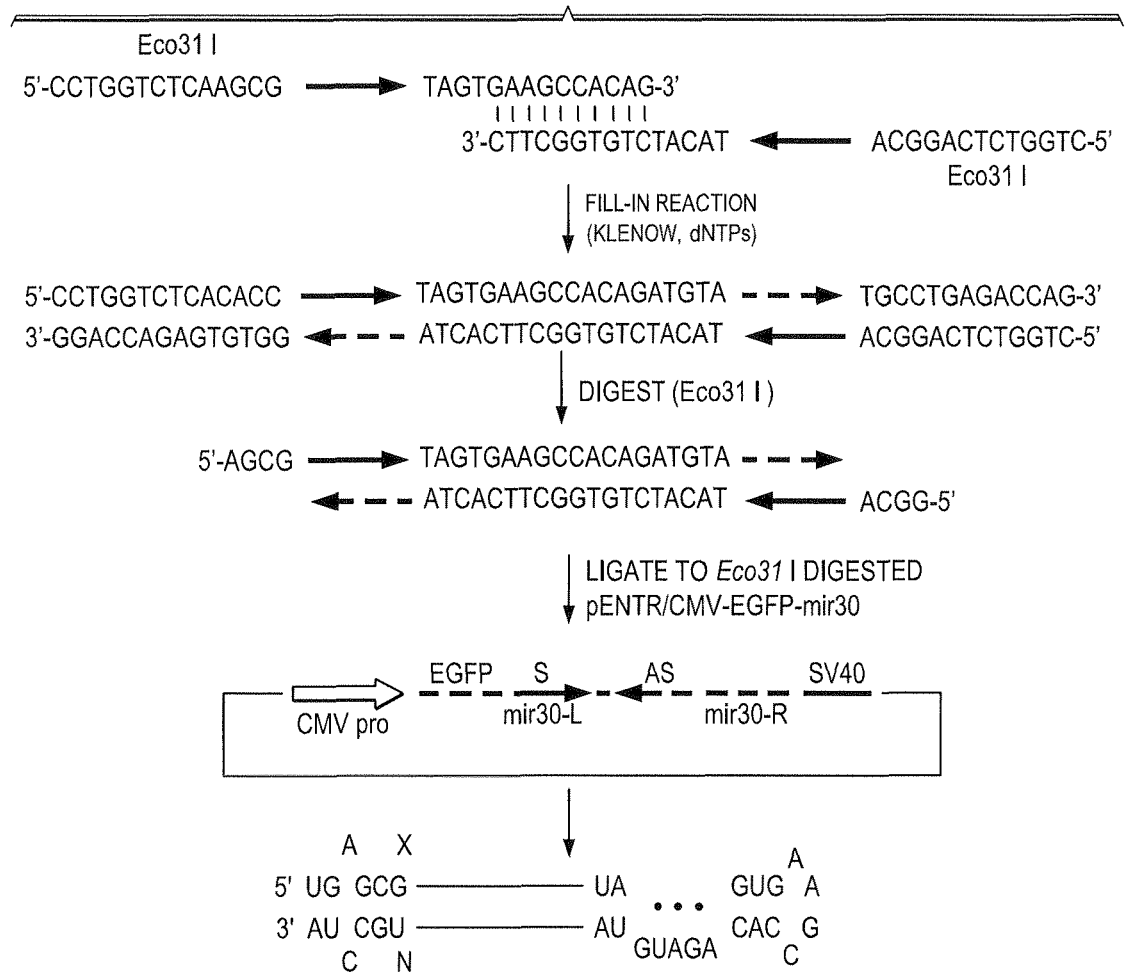
FIG. 4. Diagrams for miR-30-based shRNA template generation via the primer extension method. To reduce cost in primer synthesis, the last 10-nt sequences (5'-GAAGCCA-CAG-3', SEQ ID NO: 4) within the miR30 loop was designed as the annealing region. An Eco31 I restriction site with three protection bases was added at the 5'-end of each oligonucleotide. The cloning vector of pENTR/CMV-EGFP-miR-30 was generated by inserting a primary miR-30 fragment containing two Eco31 I sites between the EGFP coding sequence and the SV40 polyA terminal region in pENTR/CMV-EGFP vector.

The construction of miR-30-based shRNA libraries, in which the shRNAmir inserts were amplified from 97-nt synthesized oligonucleotide templates using two universal primers, has been reported (6; 41). However, according to those reports, only 25 to 60% of the clones have correct shRNA sequences even when a combination of thermostable proof-reading polymerases and PCR-enhancing agents was used. To see whether our primer-extension method can be used to construct this type of shRNA vector, we have developed a new vector with several notable features. First, we separately amplified two flanking sequences (each 125 bp) of miR-30 from human genomic DNA by PCR. A Eco31 I restriction site and 15-nt overlap sequences were introduced at the 3'-end of the left flanking sequence and the 5'-end of the right flanking sequences. A primary miR-30-based DNA fragment containing two Eco31 I sites was generated by overlap PCR and cloned into a pENTR/CMV-EGFP vector between the EGFP coding region and SV40 terminal sequences, resulting in a new pENTR/CMV-EGFP-miR-30 vector. Digestion of pENTR/CMV-EGFP-miR-30 vector with Eco31 I left 5'-CGCT and 5'-TGCC-overhangs that allowed ligation to the 5'-AGCG and 5'-GGCA overhangs of Eco31 I-digested miR-30-based shRNA inserts. For the preparation of shRNA inserts, two oligonucleotides (~50-nt in length) were designed and used in an extension reaction based on the 10-nt overlap region as shown in FIG. 4. The advantages of this primer-extension method in constructing miR-30-based shRNA vectors, compared to other methods (6), include: lower cost in synthesizing short oligonucleotides; elimination of the need for PCR amplification; no need for DNA purification before restriction enzyme digestion; and no need to introduce two artificial restriction sites within the miR-30 flanking sequences. Therefore, the resulting primary miRNA sequences are more similar to the original pri-miR-30 with the shRNA sequences being 90% correct, a much higher percentage than was achieved using other methods.

Construction of miRNA Overexpression Library

MiRNAs are endogenous approximately 22 nt RNAs that play important regulatory roles in animals and plants by targeting mRNAs for cleavage or translational repression through components shared with the RNAi pathway (3; 27; 48). Hundreds of miRNAs have been found in animals, plants and viruses. Over-expression of miRNA may facilitate the study of their normal functions and permit effective RNAi in vivo. Three different methods have been used to over-express miRNA, including chemically synthesized mimic miRNA (18), vector-based matured short-hairpin miRNA (50) or flanking sequence-included primary miRNA (47).

Figure 5:
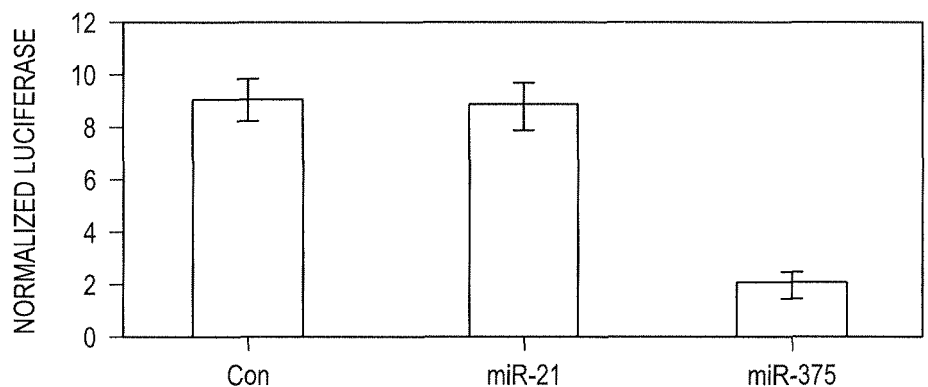
FIG. 5. Effect of miRNA expression on miRNA target-luciferase activity. 293A cells were cultured in 24-well plates. After overnight culture, cells were transfected using Lipofectamine 2000 with pGL3-miR-375, a firefly luciferase reporter construct containing one target site for miR-375, and miR-375, miR-21 expression vector or a GFP control vector expressing unrelated shRNA (Con). Twenty-four hours post-transfection, the cells were assayed for dual-luciferase activities.

To test the activity of miRNA expression vectors, we first constructed a F. luc reporter vector with the miRNA-binding site for miR-375. The binding site was made by annealing two short oligonucleotides containing the miR-375 binding site and inserting into the pGL3 vector at the Xba I restriction site, which is located between the F. luc gene and SV40 polyA terminal sequence. We tested the effect of miR-375 over-expression on suppression of gene expression by co-transfecting the miRNA over-expression vector, the F. luc reporter vector bearing the miR-375-binding site, and a transfection normalization vector, pRL-TK. Using a dual-luciferase assay, we found that the specific inhibition of the F. luc reporter gene was only observed in the cells over-expressing miR-375, not miR-21 (FIG. 5), indicating that short-hairpin-based miRNA vectors can be used to express functional miRNAs.

By using the primer-extension method, we constructed a miRNA library, which facilitates the expression of 254 matured miRNA sequences with the following features: (1) the mU6 promoter was selected to drive the expression of short-hairpin miRNA; (2) a 10-nt loop sequence of 5'-CTTC-CTGTCA-3' (SEQ ID NO: 1) was used for primer extension; (3) 5'-overlap sequences (5'-TTTG-3' and 5'-GC-3') for ligation were created by double digestion of Eco31 I and Bsp119 I; and (4) the EGFP reporter gene was included in the vector to easily track the transfection efficiency. Upon sequencing all of the plasmids, we found that only 17 out of 254 plasmids (6.7%) had mutations, further supporting the high fidelity in constructing shRNA vectors with the primer extension method of the invention. We estimate that this method could save more than 65% of the cost of methods that require oligonucleotide synthesis, plasmid preparation and DNA sequencing.

High-Throughput Screening of miRNA Involved in Survivin Promoter Activity

Survivin is a member of the apoptosis inhibitor family of proteins. It is implicated in two key biological events: control of cell proliferation and regulation of cell lifespan (29). The expression of Survivin is noted in many common tumor types but not in normal adult tissues (1; 2). Over-expression of Survivin inhibits apoptosis and promotes cancer cell survival (17). The inhibition of Survivin expression induces cell death by apoptosis (28; 39). Survivin gene expression in cancer tissue appears to be regulated transcriptionally. Several signaling pathways involved in Survivin modulation have been identified, including Sp1 transcription factor (14), TCF/β catenin (26), tumor suppressor p53 (23), Smad/BMP-7 signaling (49), P13 kinase/Akt signaling (9), Stat3 signaling (35) and IGF-1/mTOR signaling (46). Although strategies to lower Survivin levels have been pursued for rational cancer therapy, the molecular mechanisms controlling Survivin expression in tumors have not been completely elucidated (46). miRNAs are newly discovered regulators of gene expression that are implicated in many processes, such as cell proliferation, apoptosis, metabolism, cell differentiation and morphogenesis. Currently, it is not known whether miRNAs are involved in the regulation of Survivin promoter activity via various Survivin transcriptional factors. We therefore screened for potential miRNAs involved in the activation and/or inactivation of Survivin promoter activity using a miRNA over-expression library containing 254 miRNAs. To perform a quick high-throughput screen, we constructed a human Survivin promoter-driven F. luc reporter vector, pSurvivin-F.Luc, and co-transfected A549 human lung cancer cells with the miRNA over-expression library and pRL-TK normalization vector. The cells were lyzed after a 48 h after transfection for a dual-luciferase assay. Compared to the negative control vector of pCMV-mU6-shCon, any miRNA that changed Survivin promoter activity by >2-fold was considered as a hit (i.e. a positive result). Each transfection was performed in three replicates and the results are represented in FIG. 6A-F. miRNAs that had error bars inside the cutoff were not included as hits. Using these criteria, we identified 6 miRNAs that activated the Survivin promoter activity in A549 cells (miR-192, 199a, 19a, 20a, 213, and 371) and 6 miRNA that decreased Survivin promoter activity (miR-302b*, 34a, 98, 471, 381 and 463).

Figure 6G:
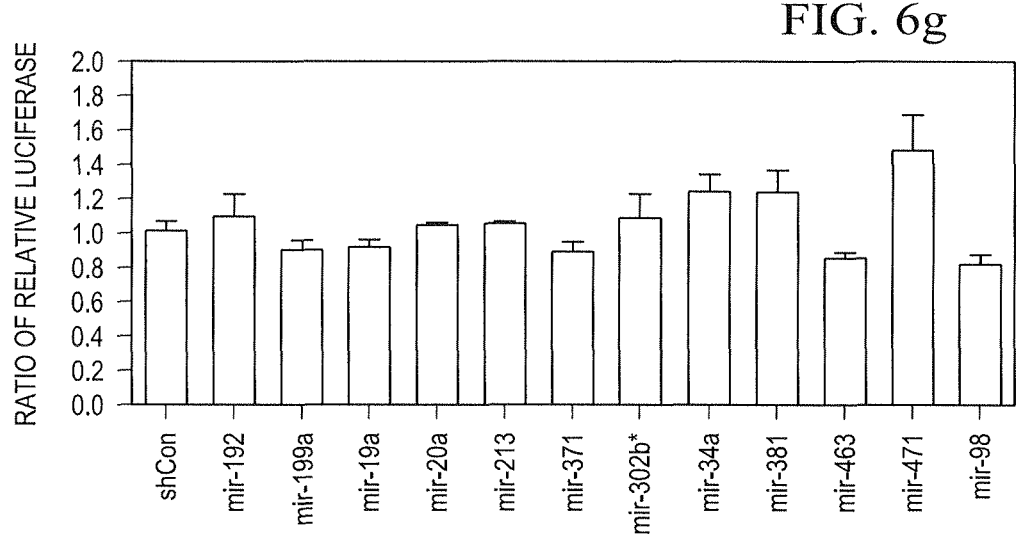

To address the specificity of the effects of miRNAs on the Survivin promoter assay, an un-related control promoter, SP-B promoter, was tested to see whether the 12 identified miRNAs affect the SP-B promoter activity in A549 cells. SP-B is a surfactant protein involved in lung surfactant function. Compared to the pEGFP/mU6-shCon vector, most of miRNAs did not change the expression of SP-B promoter-driven F. luc (FIG. 6G). Only miR-471, which down-regulated the Survivin promoter activity, modestly increased the SP-B promoter activity. This result suggests that the observed effects of miRNAs on the F. luc expression are due to the promoter activity, but are not due to a direct effect on the F. luc gene.

miRNAs are normally targeted to the 3'-UTR of a gene. In our experimental design, the 3'-UTR of Survivin was not included in the reporter construct. The effects of miRNAs on the Survivin promoter activity are likely because of the inhibition of Survivin transcriptional activators and repressors or protein(s) regulating those transcriptional factors. E2Fs promote cell death when overexpressed or when activated in response to DNA damage (34). Induction of apoptosis is a unique property of E2F1, E2F2 and E2F3 (11). It has been reported that E2Fs are involved in the Survivin transcriptional regulation, because the Survivin promoter contains an E2F-like binding element. Recent studies indicate that E2F1 is a validated target of miR-17 and miR-20a (36). miR-20a also regulates E2F2 and E2F3 via the binding sites in the 3'-UTR of their respective mRNAs (44). Therefore, it is possible that the activation of Survivin promoter activity by miR-20a may be mediated through the depression of E2F transcriptional factors.

A very interesting finding is that two miRNAs (miR-19 and miR-20) that activate the Survivin promoter belong to the miR-17-92 cluster. The miR-17-92 cluster is composed of seven miRNAs (miR-17-5p, 18, 19a, 20, 19b-1, 92-1 and 17-3p) and resides in intron 3 of the C13orf25 gene at 13q31.3. It has been observed that miR-17-92 cluster is frequently over-expressed in human cancers (20, 21). Recently, another group has reported that mir-17-92 cluster is directly regulated by c-myc (10).

Among 6 miRNAs that decreased the Survivin promoter activity, miR-34a is commonly deleted in human cancers and directly transactivated by p53 (7, 40). Inactivation of miR-34a strongly attenuates p53-mediated apoptosis, while over-expression of miR-34a mildly promotes apoptosis (40). This is consistent with our results that miR-34a decreased Survivin promoter activity.

Collectively, we demonstrated an alternative approach to construct shRNA/miRNA vectors at a greatly reduced cost with high efficacy. We estimate that this method could save over 65% of the cost of primer synthesis and DNA sequencing. It is extremely useful in generating shRNA libraries at a genome scale. We also reported the construction of a human miRNAs expression library and screening of potential miRNAs involved in Survivin gene regulation. The availability of the miRNA library as well as methods for high-throughput assay makes it possible to identify miRNAs involved in apoptosis, phagocytosis, cell proliferation, cell cycle, p53-mediated senescence, cell morphogenesis, cytokinesis and cellular signaling. This will ultimately lead to a greater understanding of the cellular processes as well as reveal key pathways that might be exploited for disease detection, prevention or treatment (8).

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

REFERENCES

1. Altieri D C. Survivin and apoptosis control. Adv Cancer Res 88: 31-52, 2003.
2. Altieri D C. Validating survivin as a cancer therapeutic target. Nat Rev Cancer 3: 46-54, 2003.
3. Bartel D P. MicroRNAs: genomics, biogenesis, mechanism, and function. Cell 116: 281-297, 2004.
4. Boden D, Pusch O, Silbermann R, Lee F, Tucker L, and Ramratnam B. Enhanced gene silencing of HIV-1 specific siRNA using microRNA designed hairpins. Nucleic Acids Res 32: 1154-1158, 2004.
5. Brummelkamp T R, Bernards R, and Agami R. A system for stable expression of short interfering RNAs in mammalian cells. Science 296: 550-553, 2002.
6. Chang K, Elledge S J, and Hannon G J. Lessons from Nature: microRNA-based shRNA libraries. Nat Methods 3: 707-714, 2006.
7. Chang T C, Wentzel E A, Kent O A, Ramachandran K, Mullendore M, Lee K H, Feldmann G, Yamakuchi M, Ferlito M, Lowenstein C J, Arking D E, Beer M A, Maitra A, and Mendell J T. Transactivation of miR-34a by p53 broadly influences gene expression and promotes apoptosis. Mol Cell 26: 745-752, 2007.
8. Cheng A M, Byrom M W, Shelton J, and Ford L P. Antisense inhibition of human miRNAs and indications for an involvement of miRNA in cell growth and apoptosis. Nucleic Acids Res 33: 1290-1297, 2005.
9. Dan H C, Jiang R, Coppola D, Hamilton A, Nicosia S V, Sebti S M, and Cheng J Q. Phosphatidylinositol-3-OH kinase/AKT and survivin pathways as critical targets for geranylgeranyltransferase I inhibitor-induced apoptosis. Oncogene 23: 706-715, 2004.
10. Dews M, Homayouni A, Yu D, Murphy D, Sevignani C, Wentzel E, Furth E E, Lee W M, Enders G H, Mendell J T, and Thomas-Tikhonenko A. Augmentation of tumor angiogenesis by a Myc-activated microRNA cluster. Nat Genet 38: 1060-1065, 2006.
11. Dimova D K, and Dyson N J. The E2F transcriptional network: old acquaintances with new faces. Oncogene 24: 2810-2826, 2005.
12. Du C, Ge B, Liu Z, Fu K, Chan W C, and McKeithan T W. PCR-based generation of shRNA libraries from cDNAs. BMC Biotechnol 6: 28, 2006.
13. Elbashir S M, Harborth J, Lendeckel W, Yalcin A, Weber K, and Tuschl T. Duplexes of 21-nucleotide RNAs mediate RNA interference in cultured mammalian cells. Nature 411: 494-498, 2001.
14. Esteve P O, Chin H G, and Pradhan S. Molecular mechanisms of trans-activation and doxorubicin mediated repression of survivin gene in cancer cells. J Biol Chem 282: 2615-2525, 2007.
15. Gou D, Jin N, and Liu L. Gene silencing in mammalian cells by PCR-based short hairpin RNA. FEBS Lett 548: 113-118, 2003.
16. Gou D, Narasaraju T, Chintagari N R, Jin N, Wang P, and Liu L. Gene silencing in alveolar type II cells using cell-specific promoter in vitro and in vivo. Nucleic Acids Res 32: e134, 2004.
17. Grossman D, Kim P J, Blanc-Brude O P, Brash D E, Tognin S, Marchisio P C, and Altieri D C. Transgenic expression of survivin in keratinocytes counteracts UVB-induced apoptosis and cooperates with loss of p53. J Clin Invest 108: 991-999, 2001.
18. Guimaraes-Sternberg C, Meerson A, Shaked I, and Soreq H. MicroRNA modulation of megakaryoblast fate involves cholinergic signaling. Leuk Res 30: 583-595, 2006.
19. Hannon G J. RNA interference. Nature 418: 244-251, 2002.
20. Hayashita Y, Osada H, Tatematsu Y, Yamada H, Yanagisawa K, Tomida S, Yatabe Y, Kawahara K, Sekido Y, and Takahashi T. A polycistronic microRNA cluster, miR-17-92, is overexpressed in human lung cancers and enhances cell proliferation. Cancer Res 65: 9628-9632, 2005.
21. He L, Thomson J M, Hemann M T, Hernando-Monge E, Mu D, Goodson S, Powers S, Cordon-Cardo C, Lowe S W, Hannon G J, and Hammond S M. A microRNA polycistron as a potential human oncogene. Nature 435: 828-833, 2005.
22. Hernandez-Hoyos G, and Alberola-Ila J. Analysis of T-cell development by using short interfering RNA to knock down protein expression. Methods Enzymol 392: 199-217, 2005.
23. Hoffman W H, Biade S, Zilfou J T, Chen J, and Murphy M. Transcriptional repression of the anti-apoptotic survivin gene by wild type p53. J Biol Chem 277: 3247-3257, 2002.
24. Kim D H, Behlke M A, Rose S D, Chang M S, Choi S, and Rossi J J. Synthetic dsRNA Dicer substrates enhance RNAi potency and efficacy. Nat Biotechnol 23: 222-226, 2005.
25. Kim J, Kim H, Lee Y, Yang K, Byun S, and Han K. A simple and economical short-oligonucleotide-based approach to shRNA generation. J Biochem Mol Biol 39: 329-334, 2006.
26. Kim P J, Plescia J, Clevers H, Fearon E R, and Altieri D C. Survivin and molecular pathogenesis of colorectal cancer. Lancet 362: 205-209, 2003.
27. Kim V N, and Nam J W. Genomics of microRNA. Trends Genet 22: 165-173, 2006.
28. Li B, Fan J, Liu X, Qi R, Bo L, Gu J, Qian C, and Liu X. Suppression of colorectal tumor growth by regulated survivin targeting. J Mol Med 84: 1077-1086, 2006.
29. Li F, Ambrosini G, Chu E Y, Plescia J, Tognin S, Marchisio P C, and Altieri D C. Control of apoptosis and mitotic spindle checkpoint by survivin. Nature 396: 580-584, 1998.
30. Luo B, Heard A D, and Lodish H F. Small interfering RNA production by enzymatic engineering of DNA (SPEED). Proc Natl Acad Sci USA 101: 5494-5499, 2004.
31. McIntyre G J, and Fanning G C. Design and cloning strategies for constructing shRNA expression vectors. BMC Biotechnol 6: 1, 2006.
32. Miyagishi M, Sumimoto H, Miyoshi H, Kawakami Y, and Taira K. Optimization of an siRNA-expression system with an improved hairpin and its significant suppressive effects in mammalian cells. J Gene Med 6: 715-723, 2004.

33. Myers J W, Jones J T, Meyer T, and Ferrell J E, Jr. Recombinant Dicer efficiently converts large dsRNAs into siRNAs suitable for gene silencing. Nat Biotechnol 21: 324-328, 2003.
34. Nahle Z, Polakoff J, Davuluri R V, McCurrach M E, Jacobson M D, Narita M, Zhang M Q, Lazebnik Y, Bar-Sagi D, and Lowe S W. Direct coupling of the cell cycle and cell death machinery by E2F. Nat Cell Biol 4: 859-864, 2002.
35. Nam S, Buettner R, Turkson J, Kim D, Cheng J Q, Muehlbeyer S, Hippe F, Vatter S, Merz K H, Eisenbrand G, and Jove R. Indirubin derivatives inhibit Stat3 signaling and induce apoptosis in human cancer cells. Proc Natl Acad Sci USA 102: 5998-6003, 2005.
36. Novotny G W, Sonne S B, Nielsen J E, Jonstrup S P, Hansen M A, Skakkebaek N E, Rajpert-De Meyts E, Kjems J, and Leffers H. Translational repression of E2F1 mRNA in carcinoma in situ and normal testis correlates with expression of the miR-17-92 cluster. Cell Death Differ 14: 879-882, 2007.
37. Paddison P J, Silva J M, Conklin D S, Schlabach M, Li M, Aruleba S, Balija V, O'Shaughnessy A, Gnoj L, Scobie K, Chang K, Westbrook T, Cleary M, Sachidanandam R, McCombie W R, Elledge S J, and Hannon G J. A resource for large-scale RNA-interference-based screens in mammals. Nature 428: 427-431, 2004.
38. Paul C P, Good P D, Winer I, and Engelke D R. Effective expression of small interfering RNA in human cells. Nat Biotechnol 20: 505-508, 2002.
39. Pyrko P, Soriano N, Kardosh A, Liu Y T, Uddin J, Petasis N A, Hofman F M, Chen C S, Chen T C, and Schonthal A H. Downregulation of survivin expression and concomitant induction of apoptosis by celecoxib and its non-cyclooxygenase-2-inhibitory analog, dimethyl-celecoxib (DMC), in tumor cells in vitro and in vivo. Mol Cancer 5: 19, 2006.
40. Raver-Shapira N, Marciano E, Meiri E, Spector Y, Rosenfeld N, Moskovits N, Bentwich Z, and Oren M. Transcriptional activation of miR-34a contributes to p53-mediated apoptosis. Mol Cell 26: 731-743, 2007.
41. Silva J M, Li M Z, Chang K, Ge W, Golding M C, Rickles R J, Siolas D, Hu G, Paddison P J, Schlabach M R, Sheth N, Bradshaw J, Burchard J, Kulkarni A, Cavet G, Sachidanandam R, McCombie W R, Cleary M A, Elledge S J, and Hannon G J. Second-generation shRNA libraries covering the mouse and human genomes. Nat Genet 37: 1281-1288, 2005.
42. Stegmeier F, Hu G, Rickles R J, Hannon G J, and Elledge S J. A lentiviral microRNA-based system for single-copy polymerase II-regulated RNA interference in mammalian cells. Proc Natl Acad Sci USA 102: 13212-13217, 2005.
43. Sui G, Soohoo C, Affar el B, Gay F, Shi Y, Forrester W C, and Shi Y. A DNA vector-based RNAi technology to suppress gene expression in mammalian cells. Proc Natl Acad Sci USA 99: 5515-5520, 2002.
44. Sylvestre Y, De Guire V, Querido E, Mukhopadhyay U K, Bourdeau V, Major F, Ferbeyre G, and Chartrand P. An E2F/miR-20a autoregulatory feedback loop. J Biol Chem 282: 2135-2143, 2007.
45. Tuschl T. Expanding small RNA interference. Nat Biotechnol 20: 446-448, 2002.
46. Vaira V, Lee C W, Goel H L, Bosari S, Languino L R, and Altieri D C. Regulation of survivin expression by IGF-1/mTOR signaling. Oncogene 2006.
47. Voorhoeve P M, le Sage C, Schrier M, Gillis A J, Stoop H, Nagel R, Liu Y P, van Duijse J, Drost J, Griekspoor A, Zlotorynski E, Yabuta N, De Vita G, Nojima H, Looijenga L H, and Agami R. A genetic screen implicates miRNA-372 and miRNA-373 as oncogenes in testicular germ cell tumors. Cell 124: 1169-1181, 2006.
48. Wang Y, Stricker H M, Gou D, and Liu L. MicroRNA: past and present. Front Biosci 12: 2316-2329, 2007.
49. Yang S, Lim M, Pham L K, Kendall S E, Reddi A H, Altieri D C, and Roy-Burman P. Bone morphogenetic protein 7 protects prostate cancer cells from stress-induced apoptosis via both Smad and c-Jun NH2-terminal kinase pathways. Cancer Res 66: 4285-4290, 2006.
50. Zeng Y, Wagner E J, and Cullen B R. Both natural and designed micro RNAs can inhibit the expression of cognate mRNAs when expressed in human cells. Mol Cell 9: 1327-1333, 2002.
51. Zhou H, Xia X G, and Xu Z. An RNA polymerase II construct synthesizes short-hairpin RNA with a quantitative indicator and mediates highly efficient RNAi. Nucleic Acids Res 33: e62, 2005.

---

What is claimed is:

1. A method for making an shRNA expression vector, comprising the steps of a. providing first and second DNA oligonucleotide primers, wherein i) said first DNA oligonucleotide primer comprises sequences encoding at a 3' end, a first RNA loop sequence;

at a 5' end, a first restriction enzyme recognition sequence; and a first RNA stem sequence, wherein in said first DNA oligonucleotide primer, said first RNA stem sequence is located between said first RNA loop sequence and said first restriction enzyme recognition sequence; and ii) said second DNA oligonucleotide primer comprises sequences encoding a second RNA loop sequence that is complementary to said first RNA loop sequence;

at a 3' end, a second restriction enzyme recognition sequence; and at a 5' end, a second RNA stem sequence, wherein said second RNA stem sequence is located between said second RNA loop sequence and said second restriction enzyme recognition sequence in said second DNA oligonucleotide primer;

b. annealing said first RNA loop sequence and said RNA loop sequence to form an annealed structure;

c. filling in single strand segments of said annealed structure to form a double-strand structure;

d. cleaving said double-strand structure using restriction enzymes that recognize said first and said second restriction enzyme recognition sequences, to form a structure with a 3' overhang and a 5' overhang; and, e. ligating said structure with a 3' overhang and a 5' overhang into an expression vector to form an shRNA expression vector;

and wherein said first RNA loop sequence and said second RNA loop sequence are 8-10 Nucleotides in length.

2. The method of claim 1, wherein said first and second DNA oligonucleotide primer each comprise 50 or fewer nucleotides.

3. The method of claim 1, wherein said first and second restriction enzyme recognition sequences are the same.

4. The method of claim 1, wherein said second RNA stem sequence is identical to said first RNA stem sequence.

* * * * *

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial
<220> FEATURE:
<223> OTHER INFORMATION: synthetic 10-nucleotide loop sequence

<400> SEQUENCE: 1
cttcctgtca                                                          10

<210> SEQ ID NO 2
<211> LENGTH: 11
<212> TYPE: DNA
<213> ORGANISM: Artificial
<220> FEATURE:
<223> OTHER INFORMATION: synthetic 11-nucleotide loop sequence

<400> SEQUENCE: 2
gtgtgctgtc c                                                        11
```

```
<210> SEQ ID NO 3
<211> LENGTH: 19
<212> TYPE: DNA
<213> ORGANISM: Artificial
<220> FEATURE:
<223> OTHER INFORMATION: synthetic 19 nucleotide loop sequence

<400> SEQUENCE: 3
tagtgaagcc acagatgta                                               19

<210> SEQ ID NO 4
<211> LENGTH: 10
<212> TYPE: DNA
<213> ORGANISM: Artificial
<220> FEATURE:
<223> OTHER INFORMATION: synthetic 10 nucleotide annealing region

<400> SEQUENCE: 4
gaagccacag                                                         10

<210> SEQ ID NO 5
<211> LENGTH: 29
<212> TYPE: DNA
<213> ORGANISM: Artificial
<220> FEATURE:
<223> OTHER INFORMATION: synthetic oligonucleotide primer; n at
      positions 16-20 represents a, t, c or g; the total number of n's
      varies from 1 to 5
<220> FEATURE:
<221> NAME/KEY: misc_feature
<222> LOCATION: (16)..(20)
<223> OTHER INFORMATION: n is a, c, g, or t

<400> SEQUENCE: 5
cctggtctca caccgnnnnn ttcaagaga                                    29

<210> SEQ ID NO 6
<211> LENGTH: 28
<212> TYPE: DNA
<213> ORGANISM: Artificial
<220> FEATURE:
<223> OTHER INFORMATION: synthetic oligonucleotide primer; n at
      positions 15-19 represents a, t, c or g; the total number of n's
      varies from 1 to 5
<220> FEATURE:
<221> NAME/KEY: misc_feature
<222> LOCATION: (15)..(19)
<223> OTHER INFORMATION: n is a, c, g, or t

<400> SEQUENCE: 6
cctggtctca aaaannnnnt ctcttgaa                                     28

<210> SEQ ID NO 7
<211> LENGTH: 20
<212> TYPE: DNA
<213> ORGANISM: Artificial
<220> FEATURE:
<223> OTHER INFORMATION: synthetic sequencing primer

<400> SEQUENCE: 7
ggactatcat atgcttaccg                                              20

<210> SEQ ID NO 8
<211> LENGTH: 32
<212> TYPE: DNA
<213> ORGANISM: Artificial
<220> FEATURE:
```

```
<223> OTHER INFORMATION: synthetic oligonucleotide primer

<400> SEQUENCE: 8
caccgcggat cgatccgacg ccgccatctc ta                              32

<210> SEQ ID NO 9
<211> LENGTH: 43
<212> TYPE: DNA
<213> ORGANISM: Artificial
<220> FEATURE:
<223> OTHER INFORMATION: synthetic oligonucleotide primer

<400> SEQUENCE: 9
cttcgaagaa ttcccgggtc tctcaaacaa ggcttttctc caa                  43

<210> SEQ ID NO 10
<211> LENGTH: 10
<212> TYPE: DNA
<213> ORGANISM: Artificial
<220> FEATURE:
<223> OTHER INFORMATION: synthetic 10 nucleotide loop sequence

<400> SEQUENCE: 10
cttcctgtca                                                       10

<210> SEQ ID NO 11
<211> LENGTH: 14
<212> TYPE: DNA
<213> ORGANISM: Artificial
<220> FEATURE:
<223> OTHER INFORMATION: segment of synthetic oligonucleotide primer

<400> SEQUENCE: 11
caaggtctca tttg                                                  14

<210> SEQ ID NO 12
<211> LENGTH: 10
<212> TYPE: DNA
<213> ORGANISM: Artificial
<220> FEATURE:
<223> OTHER INFORMATION: segment of synthetic ologonucleotide primer

<400> SEQUENCE: 12
cttcctgtca                                                       10

<210> SEQ ID NO 13
<211> LENGTH: 12
<212> TYPE: DNA
<213> ORGANISM: Artificial
<220> FEATURE:
<223> OTHER INFORMATION: segment of synthetic oligonucleotide primer

<400> SEQUENCE: 13
gagttcgaaa aa                                                    12

<210> SEQ ID NO 14
<211> LENGTH: 10
<212> TYPE: DNA
<213> ORGANISM: Artificial
<220> FEATURE:
<223> OTHER INFORMATION: segment of synthetic oligonucletoide primer

<400> SEQUENCE: 14
tgacaggaag                                                       10
```

```
<210> SEQ ID NO 15
<211> LENGTH: 20
<212> TYPE: DNA
<213> ORGANISM: Artificial
<220> FEATURE:
<223> OTHER INFORMATION: synthetic oligonucletide primer

<400> SEQUENCE: 15
acatgatagg cttggatttc                                              20

<210> SEQ ID NO 16
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 16
caccgaggcc gctggccata gaaccagaga agtga                             35

<210> SEQ ID NO 17
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 17
taactagtcc acctctgcca acgggtcccg cg                                32

<210> SEQ ID NO 18
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 18
caccgcggcc gcgtataggg ctgtctggga                                   30

<210> SEQ ID NO 19
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 19
ggactagtct gcagcctggg tac                                          23

<210> SEQ ID NO 20
<211> LENGTH: 21
<212> TYPE: DNA
<213> ORGANISM: Artificial
<220> FEATURE:
<223> OTHER INFORMATION: synthetic oligonucleotide

<400> SEQUENCE: 20
gcacaagctg gagtacaact a                                            21
```